US011653649B2

(12) United States Patent
Wenzel et al.

(10) Patent No.: US 11,653,649 B2
(45) Date of Patent: May 23, 2023

(54) ANTIMICROBIAL COMPOSITION INCLUDING A DIHYDROXAMIC ACID AND METHODS OF INHIBITING MICROBIAL GROWTH UTILIZING THE SAME

(71) Applicant: Kimberly-Clark Worldwide, Inc., Neenah, WI (US)

(72) Inventors: Scott W. Wenzel, Neenah, WI (US); Andrew R. Kischnick, Neenah, WI (US); Corey T. Cunningham, Neenah, WI (US); Vinod Chaudhary, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 7 days.

(21) Appl. No.: 16/623,427

(22) PCT Filed: Jun. 29, 2017

(86) PCT No.: PCT/US2017/039967
§ 371 (c)(1),
(2) Date: Dec. 17, 2019

(87) PCT Pub. No.: WO2019/005064
PCT Pub. Date: Jan. 3, 2019

(65) Prior Publication Data
US 2020/0120929 A1   Apr. 23, 2020

(51) Int. Cl.
| A01N 37/28 | (2006.01) |
| A01N 25/24 | (2006.01) |
| A01N 25/04 | (2006.01) |
| A01N 25/34 | (2006.01) |

(52) U.S. Cl.
CPC ............. *A01N 37/28* (2013.01); *A01N 25/04* (2013.01); *A01N 25/34* (2013.01)

(58) Field of Classification Search
None
See application file for complete search history.

(56) References Cited

U.S. PATENT DOCUMENTS

| 3,427,381 A | 2/1969 | Kirkland |
| 3,551,574 A | 12/1970 | Frohberger et al. |
| 3,629,446 A | 12/1971 | Frohberger et al. |
| 3,629,456 A | 12/1971 | Ewald et al. |
| 3,978,208 A | 8/1976 | Okada |
| 4,263,322 A | 4/1981 | van't Riet et al. |
| 4,939,299 A | 7/1990 | Coleman et al. |
| 5,206,384 A | 4/1993 | Shibahara et al. |
| 5,733,342 A | 3/1998 | Greindl et al. |
| 7,282,522 B2 | 10/2007 | Rho et al. |
| 7,323,109 B2 | 1/2008 | Bringley |
| 7,595,073 B2 | 9/2009 | Baldwin et al. |
| 8,993,641 B2 | 3/2015 | Winn |
| 2004/0265964 A1 | 12/2004 | Allen et al. |
| 2006/0211732 A1 | 9/2006 | George Hunter et al. |
| 2008/0242648 A1 | 10/2008 | Ordentlich et al. |
| 2009/0143489 A1 | 6/2009 | Winn |
| 2011/0268676 A1 | 11/2011 | Winn |
| 2015/0148421 A1 | 5/2015 | Winn |
| 2017/0172145 A1* | 6/2017 | Sherry ................. A61K 33/40 |

FOREIGN PATENT DOCUMENTS

| CN | 105935342 A | 9/2016 |
| CN | 106423574 A | 2/2017 |
| DE | 141252 A1 | 4/1980 |
| DE | 10256976 * | 6/2004 |
| DE | 10256976 A1 | 6/2004 |
| GB | 1274282 A | 5/1972 |
| JP | 49048834 A | 5/1974 |
| JP | 11189529 A2 | 7/1999 |

OTHER PUBLICATIONS

Andrews, HM, "Determination of minimum inhibitory concentrations", J Antimicrob Chemothe, 2001.*
Hase et al., "Antimicrobial Activity of Hydroxamic Acids", Chem Pharm Bull. 19(2), 1971, pp. 363-368.
Pepeljnjak et al., "Antimicrobial activity of some hydroxamic acids", Acta Pharm. 55, 2005, pp. 401-408.
Singh et al., "Synthesis and evaluation of novel hydroxamic acids as potent antibacterial and antifungal agents", Global Journal of Chemistry, vol. 1, No. 1, Apr. 23, 2015.
Mahesh et al, "Synthetic Communications: An International Journal for Rapid Communication of Synthetic Organic Chemistry", An International Journal for Rapid Communication of Synthetic Organic Chemistry, 45:7, 2014, pp. 838-846.
Majewski et al., "Syntheses and evaluation of substituted aromatic hydroxamates and hydroxamic acids that target *Mycobacterium tuberculosis*", Bioorganic & Medicinal Chemistry Letters, 2015.
Hoffman et al., "Hydroxamic Acids as a Novel Family of Serine Racemase Inhibitors: Mechanistic Analysis Reveals Different Modes of Interaction with the Pyridoxal-5'-phosphate Cofactor", J Med. Chem. 2009, 52, 6032-6041.
Kim, Sung-Kun et al., "Inhibition of Bacillus anthracis mettallo-β-lactamase by compounds with hydroxamic acid functionality." Journal of Enzyme Inhibition and Medicinal Chemistry, Aug. 24, 2016(online), vol. 31, oo, 132-137.
Elbadawi, Mohamed A. Abdallah et al., "Valproic Acid as a Potential Inhibitor of Plasmodium falciparum Histone Deacetylase 1 (PfHDAC1): An in Silico Approach", International Journal of Molecular Sciences, Feb. 11, 2015, vol. 16, pp. 3915-3931.
Andrews, HM, "Determination of minimum inhibitory concentrations", J Antimicrob Chemothe, 2001 48, pp. 5-16.

* cited by examiner

Primary Examiner — Danah Al-Awadi
(74) Attorney, Agent, or Firm — Kimberly-Clark Worldwide, Inc.

(57) ABSTRACT

Antimicrobial compositions and methods for inhibiting microbial growth are disclosed. The antimicrobial compositions can include an antimicrobial agent that includes a dihydroxamic acid having a carbon chain length less than or equal to 7.

6 Claims, 1 Drawing Sheet

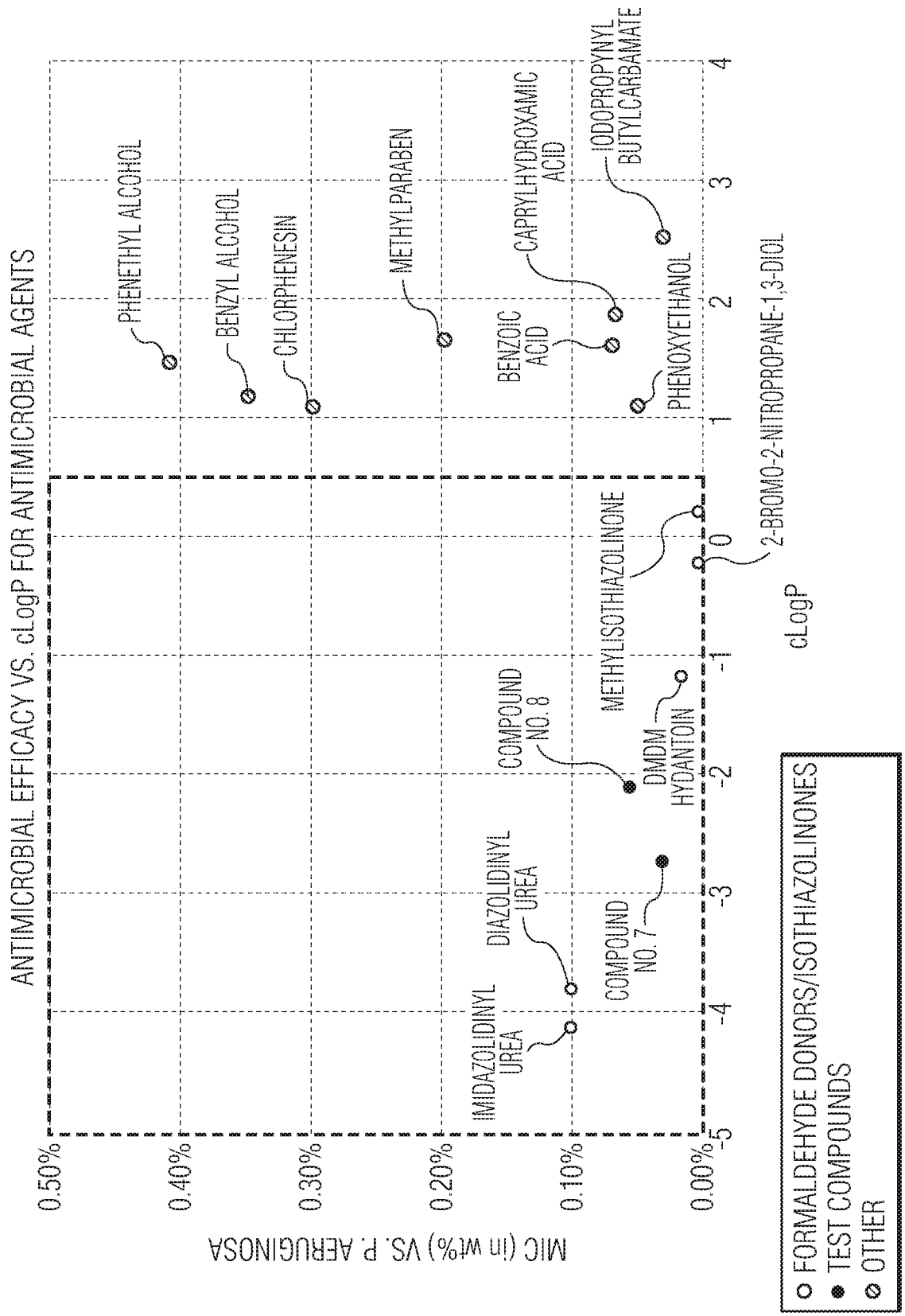

ANTIMICROBIAL COMPOSITION INCLUDING A DIHYDROXAMIC ACID AND METHODS OF INHIBITING MICROBIAL GROWTH UTILIZING THE SAME

TECHNICAL FIELD

Disclosed are antimicrobial compositions and methods of inhibiting microbial growth. More specifically, disclosed is an antimicrobial composition that includes an antimicrobial agent including a dihydroxamic acid and method of utilizing the same to inhibit microbial growth. The antimicrobial composition may be applied to or incorporated into articles such as wipes, or into solutions, ointments, lotions, creams, salves, aerosols, gels, suspensions, sprays, foams, washes, or the like.

BACKGROUND OF THE DISCLOSURE

Preservatives are an often utilized component in cosmetic, pharmaceutical, household, industrial, and personal care products to ensure that a product stays fresh on the shelf, doesn't experience spoilage, and remains free from bacterial growth. In particular, because personal care products may be used to directly contact skin or mucosa such as around body orifices where the potential for transfer of materials from the product to the consumer may be a concern, it is generally good practice to reduce contamination of the product in every possible way. The need to control microbiological growth is particularly acute in water based products such as non-ionic oil-in-water emulsions and in pre-impregnated wipes such as wet wipes.

Multiple options for antimicrobial agents that prevent microbial growth, such as formaldehyde donors or parabens, have existed throughout history and these antimicrobial agents were highly efficacious and allowed for relatively easy preservation of personal care products. Recently, traditional antimicrobial agents have been less desirable components in personal care products in view of new regulations and consumer perceptions, thus limiting the options for preventing microbial growth in certain products.

While alternative antimicrobial agents have been explored, each carry limitations. For example, some organic acids and their derivatives have been used for their antimicrobial effect, however, organic acids tend to have an inherent odor, thus limiting the concentration that can be used without negatively affecting the overall olfactory perception of the product. Additionally, organic acids often are only efficacious in the acid form, thus limiting their use to compositions having a narrow and low pH range, and also have limited water solubility. Caprylhydroxamic Acid has also been explored as an alternative antimicrobial agent and addresses some of the issues noted above (in that Caprylhydroxamic Acid does not have odor issues and is efficacious across a broader pH range), however, Caprylhydroxamic Acid has a very limited water solubility of approximately 0.14%. This limited water solubility prevents Caprylhydroxamic Acid from being used at higher percentages in compositions with limited ingredients.

Thus, there remains a need for antimicrobial compositions that include alternative antimicrobial agents that can be used in a composition to inhibit microbial growth in a product and that have lower odor, can be used in a composition over a wider pH range without losing efficacy against microbial growth, and can have greater water solubility than prior alternative antimicrobial agents.

SUMMARY OF THE DISCLOSURE

In one aspect of the disclosure, a method for inhibiting microbial growth in a product is provided. The method can include providing a composition including an antimicrobial agent. The antimicrobial agent can include a dihydroxamic acid including a carbon chain length that is less than or equal to 7. The method can further include applying the composition to the product to inhibit microbial growth.

In another aspect, a wet wipe is provided. The wet wipe can include a substrate. The wet wipe can also include a wetting composition applied to the substrate. The wetting composition can include a carrier. The carrier can include water. Water can provide between 85.0 to about 99.9% by weight of the wetting composition. The wetting composition can further include a surfactant. The wetting composition can additionally include an antimicrobial agent. The antimicrobial agent can include a dihydroxamic acid including a carbon chain length that is less than or equal to 7.

In yet another aspect, an emulsion is provided. The emulsion can include a water phase and an oil phase. The emulsion can include water. Additionally, the emulsion can include an oil. The emulsion can further include an antimicrobial agent. The antimicrobial agent can include a dihydroxamic acid including a carbon chain length that is less than or equal to 7.

DESCRIPTION OF THE DRAWINGS

FIG. 1 is a graph depicting various antimicrobial agent efficacy against *P. aeruginosa* versus their cLogP values.

DETAILED DESCRIPTION OF THE DISCLOSURE

The present disclosure is directed to antimicrobial compositions and methods of inhibiting microbial growth in which the antimicrobial compositions include a dihydroxamic acid. In particular, the disclosure is directed to antimicrobial compositions and associated methods in which the antimicrobial composition includes a dihydroxamic acid having a carbon chain length that is less than or equal to 7. The antimicrobial compositions could be utilized in a variety of cosmetic, pharmaceutical, household, industrial, and personal care products. Suitable products could include, but are not limited to: shampoo, conditioner, soaps, moisturizers, skin protective, skin restorative and skin strengthening products, hand sanitizers, skin and body cleansers, deodorants, sunscreens, lip balms, lip sticks, disinfectants, hard surface cleansers, dish soaps, laundry detergents and the like. These products could take a variety of forms including but not limited to water-thin liquids, aqueous solutions, gels, balms, lotions, ointments, suspensions, creams, milks, salves, ointments, pastes, powders, aerosols, sprays, mists, mousses, emulsions, oils, foams, washes, solid sticks, aerosols, water, oil or silicone solutions or emulsions, including water in oil, oil in water, silicone in water, water in silicone and the like. Additionally, as will be described in further detail below, the forms of these products may be used in conjunction with a substrate, such that the solution may be added to the substrate for delivery. Suitable substrate based products include, but are not limited to: wipes, facial tissue, bath tissue, paper towels, napkins, diapers, diaper pants, feminine hygiene products (tampons, pads), gloves, socks, masks or combinations thereof.

Within each of the above envisioned products, the dihydroxamic acids could be used with a variety of ingredients utilized in cosmetic, pharmaceutical, household, industrial, and personal care products. Suitable ingredients, some of which will be described in further detail herein, can come from a broad category range including, but not limited to aqueous solvents, non-aqueous solvents, humectants, emollients, surfactants, emulsifiers, builders, sequestrants, chelators, preservatives, pH modifiers, combinatorial preservatives/antimicrobial agents, disinfectants, colorants, rheology modifiers, antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, deodorants, antiperspirants, fragrance, and various other optional ingredients as are known by one skilled in the art.

Antimicrobial Agents

The antimicrobial compositions of this disclosure include an antimicrobial agent that is a dihydroxamic acid. As noted above, hydroxamic acids were known for their antimicrobial properties. Caprylhydroxamic Acid is straight chain hydroxamic acid that takes the form of a white powder. It works by being a powerful chelating agent for Iron and other beneficial metal ions. Because Caprylhydroxamic Acid has a carbon chain length of 8, it is also an optimum chain length for creating membrane disruption within microorganisms. Represented by the structure below, Caprylhydroxamic Acid is an effective preservative across a broad pH range (pH 3-7) and is advantageous to other organic acids as it maintains efficacy up to a neutral pH. Caprylhydroxamic Acid does have an inherent deficiency with water solubility, however, as it is only soluble up to 0.136% in water. As a result, it is rarely used alone and must be first solubilized in surfactants, glycols, or other solvents to be used in cosmetic formulations. Thus, compositions using Caprylhydroxamic Acid can be more complex and expensive to formulate.

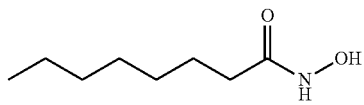

Caprylhydroxamic Acid

Initial research was conducted on hydroxamic acid derivatives by modifying the length of the carbon chain of the hydroxamic acid. Table 1 shows three hydroxamic derivatives, one with a carbon chain length of 6 (Hexylhydroxamic Acid), one with a carbon chain length of 12 (Laurylhydroxamic Acid), and one with a carbon chain length of 10 (Decylhydroxamic Acid), that were tested and compared against Caprylhydroxamic Acid. The hydroxamic acid derivative compounds were tested and compared against Caprylhydroxamic Acid in terms of their water solubility, cLogP, and their minimum inhibitory concentration ("MIC") against various bacteria and fungi. The solubility values were measured following the Determination of Aqueous Solubility by Miniaturized Shake Flask Method as discussed herein. The cLogP values listed in Table 1 were calculated using the MarvinSketch software program, version 15.6.1.0, provided by ChemAxon Ltd. (http://chemaxon.com). The settings used to calculate cLogP within that program were: Consensus Method, Cl-concentration of 0.1 mol/dm$^3$ and Na+K+ concentration of 0.1 mol/dm$^3$. It is believed that the cLogP characteristic of an antimicrobial agent plays a key role in determining the efficacy of that ingredient. If the cLogP value of a molecule is too low (that is, the molecule is too hydrophilic), it may not be able to cross the hydrophobic cell membrane and enter the cell. On the other hand, if the cLogP value of a molecule is too high (that is, the molecule is too hydrophobic), it can be difficult to solubilize in aqueous formulations. The MIC values were measured following the Anti-bacterial and Anti-fungal Minimum Inhibitory Concentration (MIC) Method as described herein.

TABLE 1

Water solubility, cLogP, and MIC values for various alkyl hydroxamic acid derivatives.

| Compound # | Name | Compound Structure | Solubility (wt %) | cLogP | MIC (%) S. Aureus | E. coli | B. cepacia | P. aeruginosa | C. albicans | A. brasiliensis |
|---|---|---|---|---|---|---|---|---|---|---|
|  | Caprylhydroxamic Acid |  | 0.1358 | 1.89 | 0.034 | 0.017 | 0.017 | 0.0679 | 0.008 | 0.004 |
| 1 | Hexylhydroxamic Acid | 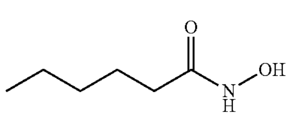 | >1.00 | 1.00 | 0.25 | 0.125 | 0.0625 | 0.0625 | 0.031 | 0.008 |
| 2 | Laurylhydroxamic Acid | 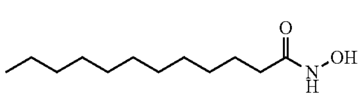 | 0.0022 | 3.67 | >0.0011* | >0.0011* | >0.0011* | >0.0011* | >0.0011* | >0.0011* |
| 3 | Decylhydroxamic Acid | 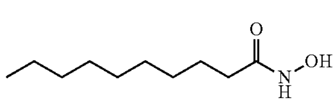 | 0.0025 | 2.78 | >0.00125* | >0.00125* | >0.00125* | >0.00125* | >0.00125* | >0.00125* |

*Actual MIC value unknown, but greater than the 1:1 dilution of the limit of solubility which was tested As can be seen in Table 1, the modifications to the carbon chain length for the hydroxamic acid derivatives Compound Nos. 1-3 were met with varied results and did not provide a compound with all the desired parameters. For example, Compound No. 1 (Hexylhydroxamic Acid) having a carbon chain length of 6 was more water soluble than Caprylhydroxamic Acid, but had lower antimicrobial efficacy in comparison to Caprylhydroxamic Acid. Compound Nos. 2 and 3 (Laurylhydroxamic Acid and Decylhydroxamic Acid), which had carbon chain lengths of 12 and 10, respectively, had poor water solubility and could not be dissolved in high enough concentration to be effective against the organisms tested.

Another class of hydroxamic acids that are known to have antimicrobial activity are the aryl hydroxamic acids. In contrast to the straight carbon chain of Caprylhydroxamic Acid, aryl hydroxamic acids contain an aromatic ring. Additional MIC and solubility testing were conducted on aryl hydroxamic acids, with results shown in Table 2.

TABLE 2

Water solubility, cLogP, and MIC results for various aryl hydroxamic acid derivatives.

| # | Compound Name | Compound Structure | Solubility (wt %) | cLogP | MIC (%) | | | | | |
|---|---|---|---|---|---|---|---|---|---|---|
| | | | | | S. Aureus | E. coli | B. cepacia | P. aeruginosa | C. albicans | A. brasiliensis |
| | Caprylhydroxamic Acid | | 0.1358 | 1.89 | 0.034 | 0.017 | 0.017 | 0.0679 | 0.008 | 0.004 |
| 5 | Benzhydroxamic Acid | 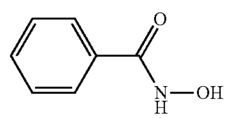 | >1.00 | 0.82 | 0.125 | 0.25 | 0.125 | 0.0625 | 0.031 | 0.016 |
| 6 | p-hydroxy Benzhydroxamic Acid | 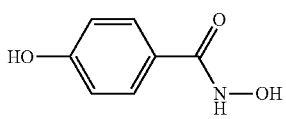 [SMILES: O=C(NO)c1ccc(O)cc1] | >1.00 | 0.52 | 0.125 | 0.0625 | 0.031 | 0.0625 | >1.00* | 0.25 |

*Actual MIC value unknown, but greater than the highest concentration tested which is listed As Table 2 shows, the aryl hydroxamic acids exhibit strong antimicrobial efficacy against a variety of organisms with greater solubility than Caprylhydroxamic Acid. However, in solution the aryl hydroxamic acids tended to generate an orange tint and an unpleasant odor. Additionally, some aryl hydroxamic acids exhibited signs of instability when added to aqueous solutions, as the orange tint of the solution became more intense over time. These factors would make aryl hydroxamic acids undesirable for use in many products.

Another class of hydroxamic acids that was studied were dihydroxamic acids. In contrast to the alkyl hydroxamic acid derivatives in Table 1 and the aryl hydroxamic acids in Table 2, dihydroxamic acids contain two hydroxamic acid functional groups within the same molecule. MIC and solubility tests were conducted on dihydroxamic acid compounds, with results shown in Table 3.

TABLE 3

Water solubility, cLogP, and MIC values for various dihydroxamic acid derivatives.

| # | Compound Name | Compound Structure | Solubility (wt %) | cLogP | MIC (%) | | | | | |
|---|---|---|---|---|---|---|---|---|---|---|
| | | | | | S. Aureus | E. coli | B. cepacia | P. aeruginosa | C. albicans | A. brasiliensis |
| | Caprylhydroxamic Acid | | 0.1358 | 1.89 | 0.034 | 0.017 | 0.017 | 0.0679 | 0.008 | 0.004 |

TABLE 3-continued

Water solubility, cLogP, and MIC values for various dihydroxamic acid derivatives.

| # | Compound Name | Compound Structure | Solubility (wt %) | cLogP | MIC (%) | | | | | |
|---|---|---|---|---|---|---|---|---|---|---|
| | | | | | S. Aureus | E. coli | B. cepacia | P. aeruginosa | C. albicans | A. brasiliensis |
| 7 | N, N',2-trihydroxybutanediamide | 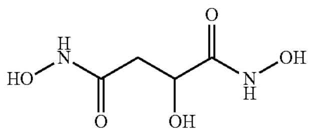 [SMILES: O=C(CC(O)C(=O)NO)NO] | >1.00 | −2.73 | 0.008 | 0.016 | 0.016 | 0.031 | 0.008 | 0.008 |
| 8 | N, N'-dihydroxysuccinamide | 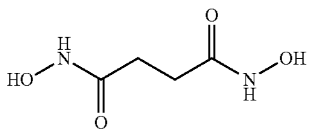 | >1.00 | −2.02 | 0.016 | 0.031 | 0.031 | 0.0625 | 0.25 | 0.031 |
| 9 | N, N'-dihydroxyoctanediamide | 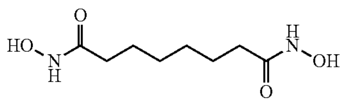 [SMILES: O=C(CCCCCCC(=O)NO)NO] | 0.248 | −0.24 | >0.124* | >0.124* | >0.124* | >0.124* | >0.124* | >0.124* |

*Actual MIC value unknown, but greater than the 1:1 dilution of the limit of solubility which was tested As noted in Table 3, there are multiple advantages to dihydroxamic acids, specifically around increasing water solubility while maintaining pH-independent antimicrobial efficacy. Compound Nos. 7 and 8 (dihydroxamic acids) have a water solubility of >1.00%. The water solubility of Compound Nos. 7 and 8 is much larger than the 0.136% water solubility of Caprylhydroxamic Acid. This is extremely important as these dihydroxamic acid derivatives can be used in cosmetic formulations without the use of surfactants, glycols, or other solvents to solubilize them. They can also be used to create formulation concentrate blends that improve manufacturing flexibility and lower shipping costs. One key advantage of the dihydroxamic acid compounds (Compound Nos. 7 and 8) is that they are able to provide strong antimicrobial efficacy at relatively low cLogP values. This enables these compounds to be effective antimicrobial agents while retaining a high degree of water solubility in aqueous systems. Compound No. 7, a dihydroxamic acid named N, N', 2-trihydroxy butane diamide, performed especially well in terms of water solubility as well as antimicrobial efficacy, outperforming Caprylhydroxamic Acid against almost all microbes tested. However, one of the dihydroxamic compounds tested (Compound No. 9), which included a carbon chain of 8, had lower water solubility and lower antimicrobial efficacy than Caprylhydroxamic Acid.

Some of the dihydroxamic acid compounds (Compound Nos. 7 and 8) also exhibited improved properties over the aryl hydroxamic acid compounds (Compound Nos. 5 and 6). Compound Nos. 7 and 8 exhibited lower MIC values, and hence stronger antimicrobial efficacy, against a variety of organisms compared to the aryl hydroxamic acids. The dihydroxamic acid compounds did not exhibit the undesirable color and odor that was observed with the aryl hydroxamic acid compounds in aqueous solution. Additionally, the dihydroxamic compounds (Compound Nos. 7 and 8) were found to have lower cLogP values than the aryl hydroxamic acids (Compound Nos. 5 and 6), indicating an even higher level of compatibility with aqueous solutions.

In addition to the impact on solubility in aqueous solutions, in emulsions, ingredients with high cLogP values have a tendency to migrate to the oil phase, where they are less available to interact with microorganisms. This tendency can result in a loss of efficacy of the antimicrobial agent. Because the dihydroxamic acids described herein have relatively low cLogP values, these ingredients are less likely to migrate to the oil phase of emulsions and are more likely to retain their antimicrobial efficacy in these systems.

Table 4 compares the cLogP values of the dihydroxamic acid compounds (Compound Nos. 7 and 8) and the aryl hydroxamic acid derivatives (Compound Nos. 5 and 6) against many of the most common formulated product antimicrobial agents as well as their MIC values against P. aeruginosa. FIG. 1 provides a chart showing the compounds of Table 4 on a graph organized by cLogP on the "x-axis" and the MIC (in wt %) against P. aeruginosa on the "y-axis," with the exception of Compound No. 9 which is not shown on FIG. 1 because the actual MIC value of Compound No. 9 is not known due to the MIC value being greater than the limit of solubility.

TABLE 4 cLogP and MIC values against P. aeruginosa for various antimicrobial agents.

| Ingredient | cLogP | MIC v. P. aeruginosa |
|---|---|---|
| Compound No. 7 | −2.73 | 0.03% |
| Compound No. 8 | −2.02 | 0.06% |
| Compound No. 9 | −0.24 | >0.12%* |
| Imidazolidinyl Urea | −4.11 | 0.10% |
| Diazolidinyl Urea | −3.79 | 0.10% |
| DMDM Hydantoin | −1.16 | 0.02% |
| 2-Bromo-2-Nitropropane-1,3-Diol | −0.19 | 0.00% |
| Methylisothiazolinone | 0.23 | 0.00% |
| Dehydroacetic Acid | 0.85 | 2.00% |
| Chlorphenesin | 1.1 | 0.30% |
| Phenoxyethanol | 1.13 | 0.05% |
| Benzyl Alcohol | 1.21 | 0.35% |
| Phenethyl Alcohol | 1.49 | 0.41% |
| Benzoic Acid | 1.63 | 0.07% |
| Methylparaben | 1.67 | 0.20% |
| Caprylhydroxamic Acid | 1.89 | 0.07% |
| Iodopropynyl Butylcarbamate | 2.54 | 0.025% |

*Actual MIC value unknown, but greater than the 1:1 dilution of the limit of solubility which was tested As can be seen from Table 4 and FIG. 1, most current antimicrobial agents have cLogP values in the range of 0.50-5.00, which means that they can be difficult to solubilize in highly aqueous solutions and can be particularly difficult to include in formulation concentrates. It is particularly unusual to find compounds with low cLogP values and strong antimicrobial efficacy (low MIC values). The only current antimicrobial agents in Table 4 that have cLogP values less than 0.50 and MIC values of less than 0.50% w/w vs. *P. aeruginosa* (as shown by the rectangle outlined by a dotted line in FIG. 1) are formaldehyde donors and Methylisothiazolinone, which have both come under public scrutiny for perceived safety concerns. In fact, these preservatives have been disallowed for use in certain types of personal care products, such as children's toiletries. On the other hand, Compound Nos. 7 and 8 (N, N',2-trihydroxy butane diamide and N,N'-dihydroxysuccinamide) have low cLogP values and strong efficacy without the accompanying safety and perception concerns of formaldehyde donors and isothiazolinones.

Similar to Table 4, Table 5 also shows the cLogP values for representative hydroxamic acid derivatives versus their MIC values against *P. aeruginosa*.

TABLE 5 cLogP and MIC values against *P. aeruginosa* for various hydroxamic acids.

| Ingredient | cLogP | MIC v. *P. aeruginosa* |
|---|---|---|
| Compound No. 5 | 0.82 | 0.06% |
| Compound No. 6 | 0.52 | 0.06% |
| Compound No. 7 | −2.73 | 0.03% |
| Compound No. 8 | −2.02 | 0.06% |
| Compound No. 9 | −0.24 | >0.12%* |
| Caprylhydroxamic Acid | 1.89 | 0.07% |
| Propylhydroxamic Acid | 0.58 | 0.50% |
| Hexylhydroxamic Acid (Compound No. 1) | 1.00 | 0.06% |
| Decylhydroxamic Acid (Compound No. 3) | 2.78 | >0.00125%* |

*Actual MIC value unknown, but greater than the 1:1 dilution of the limit of solubility which was tested As noted in Table 5, the combination of high aqueous solubility and antimicrobial efficacy demonstrated by some of the dihydroxamic acids (Compound Nos. 7 and 8) is unique even amongst the narrower class of hydroxamic acid compounds. For example, one of the best-known hydroxamic acids is Caprylhydroxamic Acid. While this compound does exhibit strong antimicrobial activity against a variety of microoganisms, it has a cLogP value of 1.89. Consequently, this material is poorly soluble in water without the addition of surfactants or other solubilizers, which greatly restricts its desirability for use in highly aqueous formulations or in formulation concentrates.

Similar performance is exhibited by other alkylhydroxamic acids. As noted in Table 5, Decylhydroxamic Acid has a cLogP value of 2.78, which is even higher than Caprylhydroxamic Acid, and is thus very difficult to utilize effectively in highly aqueous solutions. Hexylhydroxamic Acid has a lower cLogP value (1.00) than Caprylhydroxamic Acid (1.89), but it is still higher than the aryl and dihydroxamic acid derivatives. Additionally, as with many antimicrobial agents, the shorter carbon chain also results in weaker efficacy than with Caprylhydroxamic Acid. This illustrates the typical relationship between cLogP and efficacy (as cLogP decreases, efficacy also decreases), and it is expected that as the alkyl chain length is decreased further to achieve lower cLogP values, then the MIC value will be negatively affected.

By adding a second hydroxamic acid moeity, it was surprisingly discovered that the cLogP could be decreased, even below zero, while simultaneously maintaining, or even improving, antimicrobial efficacy. As a result, combinations of low cLogP and low MIC values are able to be achieved that are particularly advantageous for inhibiting microbial growth in highly aqueous solutions, solution concentrates, and emulsions. For example, hydroxamic acid compounds with cLogP of <0.50 and MIC values of <0.50% w/w for *P. aeruginosa* can be obtained. Even more preferably, hydroxamic acid compounds with cLogP of <0 and MIC values of <0.50% w/w for *P. aeruginosa* can be obtained. Still more preferably, hydroxamic acid compounds with cLogP of <−1.00 and MIC values of <0.50% w/w for *P. aeruginosa* can be obtained. This combination of low cLogP and low MIC value has been previously unknown outside of formaldehyde donating preservatives and isothiazolinones, both of which are undesirable to use in cosmetics due to regulatory and consumer perception issues. The combination of low cLogP values and low MIC values provides exceptional flexibility to achieve adequate inhibition of microbial growth of highly aqueous formulations, formulation concentrates, and emulsions.

While adding a second hydroxamic acid functional group improves both efficacy and solubility relative to compounds with a single hydroxamic acid group, not all dihydroxamic acids exhibit the highly desirable combination of high solubility and strong broad-spectrum efficacy of Compound Nos. 7 and 8. For example, Compound No. 9 (N, N'-dihydroxyoctanediamide), which has a longer carbon chain between the two hydroxamic acid groups, exhibited significantly lower solubility and efficacy (higher MIC values) compared to Compound Nos. 7 and 8. This indicates that carbon chain length plays a key role in determining solubility and efficacy of dihydroxamic acids, and that compounds with a carbon chain length of less than 8 (including both hydroxamic acid carbons) are preferred.

Antimicrobial Efficacy Testing, as described in the Test Methods section herein, was completed on various test formulations including dihydroxamic acid derivatives, such as Compound No. 7 (N, N',2-trihydroxy butane diamide) as well as other dihydroxamic acid derivatives. The following eight Exemplary Compositions show the formulation as well as the Antimicrobial Efficacy Testing results.

Exemplary Composition No. 1:
0.16% N,N',2-trihydroxy butane diamide (Compound No. 7)
85.89% Water
13.95% 0.1 N HCl
pH=4.50

TABLE 6

Antimicrobial Efficacy Testing results for Exemplary Composition No. 1.

| Organism | Initial | Day 7 | Day 14 | Day 28 |
|---|---|---|---|---|
| | CFU/gram or mL | | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | 115 | <10 | <10 |
| A. brasiliensis | 6.8E+05 | 115,000 | 90,000 | 800 |
| B. cepacia | 3.8E+05 | 700 | <10 | <10 |

As can be seen from results in Table 6, Exemplary Composition No. 1 that included the dihydroxamic acid derivative N,N',2-trihydroxy butane diamide was effective at inhibiting growth of various bacteria and fungi.

Exemplary Composition No. 2

0.32% N,N',2-trihydroxy butane diamide (Compound No. 7)

24.68% 0.1 N HCl 75.00% Water pH=4.46

TABLE 7

Antimicrobial Efficacy Testing results for Exemplary Composition No. 2.

| Organism | Initial | Day 7 | Day 14 | Day 28 |
|---|---|---|---|---|
| | | CFU/gram or mL | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | <10 | <10 | <10 |
| A. brasiliensis | 6.8E+05 | 31,500 | 1,550 | <100 |
| B. cepacia | 3.8E+05 | <10 | <10 | <10 |

As can be seen from results in Table 7, Exemplary Composition No. 2 that included the dihydroxamic acid derivative N,N',2-trihydroxy butane diamide was effective at inhibiting growth of various bacteria and fungi.

Exemplary Composition No. 3

0.15% N, N'-dihydroxysuccinamide (Compound No. 8)

0.18% 0.1 N HCl 99.67% Water pH=4.50

TABLE 8

Antimicrobial Efficacy Testing results for Exemplary Composition No. 3.

| Organism | Initial | Day 7 | Day 14 | Day 28 |
|---|---|---|---|---|
| | | CFU/gram or mL | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | <10 | <10 | <10 |
| A. brasiliensis | 6.8E+05 | 1,550 | <100 | <100 |
| B. cepacia | 3.8E+05 | 105 | <10 | <10 |

As can be seen from results in Table 8, Exemplary Composition No. 3 that included dihydroxamic acid derivative N, N'-dihydroxysuccinamide was effective at inhibiting growth of various bacteria and fungi. It is noted that N, N'-dihydroxysuccinamide has a carbon chain length of 4, similar to N,N',2-trihydroxy butane diamide (Compound No. 7), discussed above.

Exemplary Composition No. 4

0.30% N, N'-dihydroxysuccinamide (Compound No. 8)

0.27% 0.1 N HCl 99.43% Water pH=4.54

TABLE 9

Antimicrobial Efficacy Testing results for Exemplary Composition No. 4.

| Organism | Initial | Day 7 | Day 14 | Day 28 |
|---|---|---|---|---|
| | | CFU/gram or mL | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | <10 | <10 | <10 |
| A. brasiliensis | 6.8E+05 | <100 | <100 | <100 |
| B. cepacia | 3.8E+05 | <10 | <10 | <10 |

As can be seen from results in Table 9, Exemplary Composition No. 4 that included the dihydroxamic acid derivative N, N'-dihydroxysuccinamide was effective at inhibiting growth of various bacteria and fungi.

Exemplary Composition No. 5

0.41% N, N'-dihydroxyoctanediamide (Compound No. 9)

0.41% Tagat CH40 (PEG-40 Hydrogenated Castor Oil)

99.18% Water pH=4.50

TABLE 10

Antimicrobial Efficacy Testing results for Exemplary Composition No. 5.

| Organism | Initial | Day 7 | Day 14 | Day 28 |
|---|---|---|---|---|
| | | CFU/gram or mL | | |
| S. aureus | 4.5E+05 | >2500 | N/A | N/A |
| E. coli | 3.9E+05 | >2500 | N/A | N/A |
| P. aeruginosa | 3.2E+05 | >2500 | N/A | N/A |
| C. albicans | 3.9E+05 | >25000 | N/A | N/A |
| A. brasiliensis | 6.8E+05 | >2500000 | N/A | N/A |
| B. cepacia | 3.8E+05 | >2500 | N/A | N/A |

As shown in Table 10, surprisingly, Exemplary Composition No. 5 that included the dihydroxamic acid derivative N, N'-dihydroxyoctanediamide was not effective at inhibiting growth of various bacteria and fungi. The Antimicrobial Efficacy Testing was discontinued after Day 7 due to a high degree of sample contamination. The dihydroxamic acid N, N'-dihydroxyoctanediamide includes a carbon chain of 8.

Exemplary Composition No. 6

98.16% Water 0.64% Plantapon LGC Sorb (Lauryl Glucoside and Sodium Lauryl Glucose Carboxylate)

0.30% Eumulgin SML-20 (Polysorbate 20)

0.30% Zemea (Propanediol)

0.32% N,N' 2-trihydroxy butane diamide (Compound No. 7)

0.28% Malic Acid pH=4.50

TABLE 11

Antimicrobial Efficacy Testing results for Exemplary Composition No. 6.

| Organism | Initial | Day 7 | Day 14 | Day 28 |
|---|---|---|---|---|
| | | CFU/gram or mL | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | <10 | <10 | <10 |
| A. brasiliensis | 6.8E+05 | <100 | <100 | <100 |
| B. cepacia | 3.8E+05 | <10 | <10 | <10 |

As can be seen from results in Table 11, Exemplary Composition No. 6 that included the dihydroxamic acid N,N',2-trihydroxy butane diamide (Compound No. 7) was effective at inhibiting growth of various bacteria and fungi. Exemplary Composition No. 6 includes a sample formulation that included various other components other than the antimicrobial agent such as nonionic and anionic surfactants (Lauryl Glucoside and Sodium Lauryl Glucose Carboxylate), a non-ionic emulsifier (Polysorbate 20), humectant (Propanediol), and a pH adjusting ingredient (Malic Acid).

Exemplary Composition No. 6 Applied to a Coform Basesheet at 300% Add-on

Exemplary Composition No. 6 (as noted above) was applied to a coform basesheet at 300% and the wipe including the wetting composition was run through the Antimicrobial Effectiveness Testing. Table 12 shows the results.

TABLE 12

Antimicrobial Efficacy Testing results for Exemplary Composition No. 6 applied to a coform basesheet.

| Organism | Initial | Day 7 | Day 14 | Day 28 |
|---|---|---|---|---|
| | CFU/gram or mL | | | |
| S. aureus | 9.0E+05 | <10 | <10 | <10 |
| E. coli | 7.9E+05 | <10 | <10 | <10 |
| P. aeruginosa | 6.3E+05 | <10 | <10 | <10 |
| C. albicans | 7.7E+05 | 8,450 | <10 | <10 |
| A. brasiliensis | 1.4E+06 | <100 | <100 | <100 |
| B. cepacia | 7.5E+05 | <10 | <10 | <10 |

As can be seen from results in Table 12, a wipe including the wetting composition of Exemplary Composition No. 6 was effective at inhibiting growth of various bacteria and fungi.

Exemplary Composition No. 7

TABLE 13

Exemplary Composition No. 7.

| Trade Name | INCI Name | Manufacturer | % Wt |
|---|---|---|---|
| Water | Water | | 72.060 |
| Jaguar Optima | Guar Hydroxypropyltrimonium Chloride | Solvay | 0.200 |
| Compound No. 7 (N,N',2-trihydroxy butane diamide) | | | 0.320 |
| Rhodapex EXB 70 NAT | Sodium Laureth Sulfate | Solvay | 14.860 |
| Mackam 35UL HA | Cocamidopropyl Betaine | Solvay | 10.000 |
| Dehyquart cc7 BZ | Polyquaternium-7 | BASF | 0.460 |
| Dissolvine GL-47 | Tetrasodium Glutamate Diacetate | Akzo Nobel | 0.400 |
| Citric Acid F6000 | Citric Acid | Jungbunzlauer | 0.800 |
| NaCl | Sodium Chloride | | 0.900 |
| Total | | | 100.000 |

*Adjusted pH to 4.10

TABLE 14

Antimicrobial Efficacy Testing results for Exemplary Composition No. 7.

| Organism | Initial | Day 7 | Day 14 | Day 28 |
|---|---|---|---|---|
| | CFU/gram or mL | | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | <10 | <10 | <10 |
| A. brasiliensis | 6.8E+05 | <100 | <100 | <100 |
| B. cepacia | 3.8E+05 | <10 | <10 | <10 |

As can be seen from Table 14, Exemplary Composition No. 7 that included the dihydroxamic acid N,N',2-trihydroxy butane diamide (Compound No. 7) was effective at inhibiting growth of various bacteria and fungi. Exemplary Composition No. 7 provides an exemplary wash composition, which has a weight percentage of Water (i.e., 72.060% by weight of the composition) and included various ingredients common to a wash composition other than an antimicrobial agent, such as an anionic surfactant (Sodium Laureth Sulfate), a surfactant (Cocamidopropyl Betaine), a cationic surfactant (Polyquaternium-7), and a chelating agent (Tetrasodium Glutamate Diacetate).

Exemplary Composition No. 8

TABLE 15

Exemplary Composition No. 8.

| Trade Name | INCI Name | Manufacturer | % Wt |
|---|---|---|---|
| Water | Water | | 91.030 |
| Jaguar S | Guar Gum | Solvay | 0.085 |
| Protanal Ester BV 3750 | Propylene Glycol Alginate | FMC Biopolymer | 0.165 |
| Cetiol 868 | Ethylhexyl Stearate | BASF | 1.000 |
| PMX-200 Fluid (100 cst) | Dimethicone | Xiameter | 1.500 |
| Ceralution H | Behenyl Alcohol, Glyceryl Stearate, Glyceryl Stearate Citrate, Disodium Ethylene Dicocamide PEG-15 Disulfate | Sasol | 2.000 |
| Glycerin USP | Glycerin | Spectrum | 3.000 |
| Rhodicare XC | Xanthan Gum | Solvay | 0.250 |
| Compound No. 7 (N,N'2-trihydroxy butane diamide) | | | 0.320 |
| Trisodium Citrate Dihydrate | Sodium Citrate | Jungbunzlauer | 0.650 |
| Citric Acid F6000 | Citric Acid | Jungbunzlauer | q.s.* |
| Total | | | 100.000 |

*Adjust pH to 4.50

TABLE 16

Antimicrobial Efficacy Testing results
for Exemplary Composition No. 8.

| Organism | Initial | Day 7 | Day 14 | Day 28 |
|---|---|---|---|---|
| | | CFU/gram or mL | | |
| S. aureus | 4.5E+05 | <10 | <10 | <10 |
| E. coli | 3.9E+05 | <10 | <10 | <10 |
| P. aeruginosa | 3.2E+05 | <10 | <10 | <10 |
| C. albicans | 3.9E+05 | <10 | <10 | <10 |
| A. brasiliensis | 6.8E+05 | 80,000 | 2,250 | <100 |
| B. cepacia | 3.8E+05 | <10 | <10 | <10 |

As noted in Table 16, Exemplary Composition No. 8 that included the dihydroxamic acid N,N',2-trihydroxy butane diamide (Compound No. 7) was effective at inhibiting growth of various bacteria and fungi. Exemplary Composition No. 7 provides an exemplary emulsion including an antimicrobial agent and other common emulsion components, such as an emulsifier (Propylene Glycol Alginate), thickeners (Guar Gum and Xanthan Gum), an oil (Ethylhexyl Stearate), an emollient (Dimethicone), and Glycerin.

From the MIC testing and Antimicrobial Efficacy Testing, it was surprisingly found that not all dihydroxamic acids provide a satisfactory antimicrobial effect. As shown in Exemplary Composition No. 5, the dihydroxamic acid of N, N'-dihydroxyoctanediamide (Compound No. 9) did not pass the Antimicrobial Efficacy Testing and the test was discontinued after high sample contamination. In comparison with the other Exemplary Compositions which included dihydroxamic acids having shorter carbon chain length (i.e., carbon chain lengths of 4), it is believed that dihydroxamic acids having a carbon chain of less than 8 will provide satisfactory water solubility yet still remain effective at inhibiting microbial growth.

Thus, it is envisioned that various modifications can be made to dihydroxamic acids that can demonstrate the advantages of high water solubility and efficacy against a broad spectrum of bacteria and fungi. For example, it is envisioned that the dihydroxamic acids could include a carbon chain length of less than 8, preferably less than or equal to 6, and even more preferably less than or equal to 4. The dihydroxamic acid can have a formula as follows:

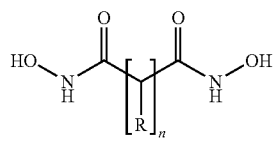

where n is a number between 0 and 5, inclusive, and R (referred to as an "R group") is independently selected for each repeat unit in the carbon chain and can be any one of H (hydrogen), OH (hydroxyl group), CH₃ (methyl group), and any halogen. For example, in one preferred embodiment, at least one R group in the dihydroxamic acid can be an OH. In some embodiments, each R group in the dihydroxamic acid can either be H or OH.

Some embodiments of the antimicrobial compositions of the present disclosure can be suitably made with a dihydroxamic acid in an amount of from about 0.001% (by the total weight of the composition) to about 5% (by total weight of the composition), or preferably from about 0.01% (by total weight of the composition) to about 3% (by total weight of the composition), or more preferably from about 0.01% (by total weight of the composition) to about 1.0% (by total weight of the composition).

Carriers

The antimicrobial compositions of the present disclosure may be formulated with one or more conventional and compatible carrier materials. The antimicrobial composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic, pharmaceutical, and medical arts as a basis for ointments, lotions, creams, salves, aerosols, gels, suspensions, sprays, foams, washes, and the like, and may be used in their established levels. The carrier can comprise from about 0.01% to about 99.98% (by total weight of the composition), depending on the carrier used.

Preferable carrier materials include polar solvent materials, such as water. Other potential carriers include emollients, humectants, polyols, surfactants, esters, perfluorocarbons, silicones, and other pharmaceutically acceptable carrier materials. In one embodiment, the carrier is volatile, allowing for immediate deposition of the antimicrobial ingredient to the desired surface while improving overall usage experience of the product by reducing drying time. Non-limiting examples of these volatile carriers include 5 cst Dimethicone, Cyclomethicone, Methyl Perfluoroisobutyl Ether, Methyl Perfluorobutyl Ether, Ethyl Perfluoroisobutyl Ether and Ethyl Perfluorobutyl Ether. Unlike conventional volatile carriers such as ethanol or isopropyl alcohol, these carriers have no antimicrobial effect.

In one embodiment, the antimicrobial compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, fatty acids, glycerol esters and derivatives, propylene glycol esters and derivatives, alkoxylated carboxylic acids, alkoxylated alcohols, fatty alcohols, and combinations thereof.

Some embodiments of the antimicrobial compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In some embodiments, the antimicrobial compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. The fatty acids can include, but are not limited to, capric acid, undecylenic acid, lauric acid, Myristic acid, palmitic acid, stearic acid, oleic acid, linoleic acid, arachidic acid, and behenic acid. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the antimicrobial compositions or the present disclosure are listed in the *International Cosmetic Ingredient Dictionary and Handbook*, 11th Edition, CTFA, (January, 2006) ISBN-10: 1882621360, ISBN-13: 978-1882621361, and in the 2007 *Cosmetic Bench Reference*, Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the antimicrobial compositions of the present disclosure include, for example, glycerin, glycerin derivatives, hyaluronic acid, hyaluronic acid derivatives, betaine, betaine derivatives, amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof.

The antimicrobial compositions of the disclosure may include one or more humectants in an amount of about 0.01% (by total weight of the composition) to about 20% (by total weight of the composition), or about 0.05% (by total weight of the composition) to about 10% by total weight of the composition), or about 0.1% (by total weight of the composition) to about 5.0% (by total weight of the composition).

The antimicrobial compositions may include water. For instance, where the antimicrobial composition is a wetting composition, such as described below for use with a wet wipe, the composition will typically include water. The antimicrobial compositions can suitably comprise water in an amount of from about 0.01% (by total weight of the composition) to about 99.98% (by total weight of the composition), or from about 1.00% (by total weight of the composition) to about 99.98% (by total weight of the composition), or from about 50.00% (by total weight of the composition) to about 99.98% (by total weight of the composition), or from about 75.00% (by total weight of the composition) to about 99.98% (by total weight of the composition). In some embodiments, water can comprise an amount from about 50.00% (by total weight of the composition) to about 70.00% (by total weight of the composition). In some embodiments, water can comprise an amount greater than 90.00% (by total weight of the composition).

In an embodiment where the antimicrobial composition serves as a wash (e.g. shampoo; surface cleaner; or hand, face, or body wash), the antimicrobial composition will likely include one or more surfactants. In an embodiment where the antimicrobial composition is included in a wipe, the antimicrobial composition may also likely include one or more surfactants. These may be selected from anionic, cationic, nonionic, zwitterionic, and amphoteric surfactants. Amounts of surfactants may range from 0.01 to 30%, or from 10 to 30%, or from 0.05 to 20%, or from 0.10 to 15% by total weight of the composition. In some embodiments, such as when the wetting composition is used with a wipe, the surfactant can comprise less than 5% by total weight of the wetting composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counter-ions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternised amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and trid tridecanol ethoxylates.

Suitable zwitterionic surfactants include, for example, alkyl amine oxides, alkyl hydroxysultaines, silicone amine oxides, and combinations thereof. Specific examples of suitable zwitterionic surfactants include, for example, 4-[N, N-di(2-hydroxyethyl)-N-octadecylammonio]-butane-1-carboxylate, S—[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N- dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, lauryl hydroxysultaine and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amnphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the antimicrobial compositions. Suitable rheology modifiers are compatible with the antimicrobial agent. As used herein, "compatible" refers to a compound that, when mixed with the antimicrobial agent, does not adversely affect the antimicrobial properties of same.

A thickening system is used in the antimicrobial compositions to adjust the viscosity and stability of the compositions. Specifically, thickening systems prevent the composition from running off of the hands or body during dispensing and use of the composition. When the antimicrobial composition is used with a wipe product, a thicker formulation can be used to prevent the composition from migrating from the wipe substrate.

The thickening system should be compatible with the compounds used in the present disclosure; that is, the thickening system, when used in combination with the antimicrobial compounds, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include but are not limited to hydroxethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for a composition having a viscosity in the range of greater than 1 cP to about 30,000 cP or more. In another embodiment, the thickeners provide compositions having a viscosity of from about 100 cP to about 20,000 cP. In yet another embodiment, thickeners provide compositions having a viscosity of from about 200 cP to about 15,000 cP. In embodiments where the compositions are included in a wipe, the viscosity may range from about 1 cP to about 2000 cP. In some embodiments, it is preferable to have a viscosity of the composition be less than 500 cP.

Typically, the antimicrobial compositions of the present disclosure include the thickening system in an amount of no more than about 20% (by total weight of the composition), or from about 0.01% (by total weight of the composition) to about 20% (by total weight of the composition). In another aspect the thickening system is present in the antimicrobial composition in an amount of from about 0.10% (by total weight of the composition) to about 10% (by total weight of the composition), or from about 0.25% (by total weight of the composition) to about 5% (by total weight of the composition), or from about 0.5% (by total weight of the composition) to about 2% (by total weight of the composition).

Emulsifiers

In one embodiment, the antimicrobial compositions may include hydrophobic and hydrophilic ingredients, such as a lotion or cream. Generally, these emulsions have a dispersed phase and a continuous phase, and are generally formed with the addition of a surfactant or a combination of surfactants with varying hydrophilic/lipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, lsosteareth-20, Laureth-23, Laureth-4, Lecithin, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, Ill.)); ARLACEL LC (INCI: Sorbitan Stearate (and) Sorbityl Laurate, commercially available from Croda (Edison, N.J.)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, N.J.)); UNIOX CRISTAL (INCI: Cetearyl Alcohol (and) Polysorbate 60 (and) Cetearyl Glucoside, commercially available from Chemyunion (São Paulo, Brazil)). Other suitable emulsifiers include lecithin, hydrogenated lecithin, lysolecithin, phosphatidylcholine, phospholipids, and combinations thereof.

Adjunct Ingredients

The antimicrobial compositions of the present disclosure may additionally include adjunct ingredients conventionally found in cosmetic, pharmaceutical, medical, household, industrial, or personal care compositions/products in an established fashion and at established levels. For example, the antimicrobial compositions may comprise additional compatible pharmaceutically active and compatible materials for combination therapy, such as antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the antimicrobial compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents (e.g., water soluble glycol and glycol ethers, glycerin, water soluble polyethylene glycols, water soluble polyethylene glycol ethers, water soluble polypropylene glycols, water soluble polypropylene glycol ethers, dimethylisosorbide), solubilizing agents, suspending agents, builders, (e.g., alkali and alkaline earth metal salts of carbonate, bicarbonate, phosphate, hydrogen phosphate, dihydrogen phosphate, sulfate hydrogen sulfate), wetting agents, pH adjusting ingredients (a suitable pH range of the compositions can be from about 3.5 to about 8), chelators, propellants, dyes and/or pigments, and combinations thereof.

Another component that may be suitable for addition to the antimicrobial compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the antimicrobial compositions include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

In addition to the antimicrobial agents discussed herein, the antimicrobial composition may include various combinatorial antimicrobial agents to increase shelf life. Some suitable combinatorial antimicrobial agents that may be used in the present disclosure include traditional antimicrobial agents. As used herein, "traditional antimicrobial agents" means compounds that have been historically recognized by regulatory bodies as providing an antimicrobial effect, such as those listed in the European Union's Annex V list of preservatives allowed in cosmetics products. Traditional antimicrobial agents include, but are not limited to: propionic acid and salts thereof; salicylic acid and salts thereof; sorbic acid and salts thereof; benzoic acid and salts and esters thereof; formaldehyde; paraformaldehyde; o-phenylphenol and salts thereof; zinc pyrithione; inorganic sulfites; hydrogen sulfites; chlorobutanol; benzoic parabens, such as methylparaben, propylparaben, butylparaben, ethylparaben, isopropylparaben, isobutylparaben, benzylparaben, sodium methylparaben and sodium propylparaben; dehydroacetic acid and salts thereof; formic acid and salts thereof; dibromohexamidine isethionate; thimerosal; phenylmercuric salts; undecylenic acid and salts thereof; hexetidine; 5-bromo-5-nitro-1,3-dioxane; 2-bromo-2-nitropropane-1,3,-diol; dichlorobenzyl alcohol; triclocarban; p-chloro-m-cresol; triclosan; chloroxylenol; imidazolidinyl urea; polyaminopropyl biguanide; phenoxyethanol, methenamine; quaternium-15; climbazole; DMDM hydantoin; benzyl alcohol; piroctone olamine; bromochlorophene; o-cymen-5-ol; methylchloroisothiazolinone; methylisothiazolinone; chlorophene; chloroacetamide; chlorhexidine; chlorhexidine diacetate; chlorhexidine digluconate; chlorhexidine dihydrochloride; phenoxyisopropanol; alkyl (C12-C22) trimethyl ammonium bromide and chlorides; dimethyl oxazolidine; diazolidinyl urea; hexamidine; hexamidine diisethionate; glutaral; 7-ethylbicyclooxazolidine; chlorphenesin; sodium hydroxymethylglycinate; silver chloride; benzethonium chloride; benzalkonium chloride; benzalkonium bromide; benzylhemiformal; iodopropynyl butylcarbamate; ethyl lauroyl arginate HCl; citric acid and silver citrate.

Other combinatorial antimicrobial agents that may be added to the antimicrobial compositions of the present disclosure include non-traditional antimicrobial agents that are known to exhibit antimicrobial effects in addition to their primary functions, but that have not historically been recognized as antimicrobial agents by regulatory bodies (such as on the European Union's Annex V list). Examples of these non-traditional antimicrobial agents include, but are not limited to, hydroxyacetophenone, caprylyl glycol, sodium coco-PG dimonium chloride phosphate, phenylpropanol, lactic acid and salts thereof, caprylhydroxamic acid, levulinic acid and salts thereof, sodium lauroyl lactylate, phenethyl alcohol, sorbitan caprylate, glyceryl caprate, glyceryl caprylate, ethylhexylglycerin, p-anisic acid and salts thereof, gluconolactone, decylene glycol, 1,2-hexanediol, glucose oxidase and lactoperoxidase, leuconostoc/radish root ferment filtrate and glyceryl laurate.

The amount of the combinatorial antimicrobial agents in the antimicrobial compositions is dependent on the relative amounts of other components present within the composition. For example, in some embodiments, the combinatorial antimicrobial agent can be present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition). In some embodiments, the combinatorial antimicrobial agent can be present in the composition in an amount less than 0.2% (by total weight of the composition).

However, in some embodiments, the antimicrobial composition is substantially free of any combinatorial antimicrobial agent, yet still provides adequate efficacy against microbial growth. Thus, in some embodiments, the antimicrobial composition does not include a traditional antimicrobial agent or a non-traditional antimicrobial agent. These embodiments can provide the benefit of simpler formulations and improved consumer appeal.

Delivery Vehicles

The antimicrobial compositions of the present disclosure may be used in combination with a product that can serve as a delivery vehicle for the antimicrobial composition. For example, the antimicrobial composition may be incorporated into or onto a substrate, such as a wipe substrate, an absorbent substrate, a fabric or cloth substrate, a tissue or paper towel substrate, or the like. In one embodiment, the antimicrobial composition may be used in combination with a wipe substrate to form a wet wipe or may be a wetting composition for use in combination with a wipe which may be dispersible. In other embodiments, the antimicrobial composition may be incorporated into wipes such as wet wipes, hand wipes, face wipes, cosmetic wipes, cloths and the like. In yet other embodiments, the antimicrobial compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a non-woven material that is wetted with an aqueous solution termed the "wetting composition," which may include or be composed entirely of the antimicrobial compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

In some embodiments when the antimicrobial composition is used as a wetting composition with a substrate, the wetting composition can be applied to the substrate at an add-on percentage of from about 30% to about 500%, or from about 125% to about 400%, or from about 150% to about 350%.

TEST METHODS

Determination of Aqueous Solubility (pH-4.5) by Miniaturized Shake Flask Method
 Test Media: Ultrapure water (pH-4.5) (18MΩDl water)
 Test Concentration: 10 mg/ml
 Incubation Details: 22° C. +/−3° C.
 Method of Analysis: Photometric analysis using Microplate reader
 Data Output: Aqueous Solubility
Study Procedure:
Preparation of 0.1 M Citric Acid Monohydrate Solution
 Approximately, 1.050 g of citric acid monohydrate was weighed and dissolved in 50 mL of ultrapure water. The solution was transferred to 50 mL tube and stored at room temperature (22° C.±3° C.).
Preparation of 0.1 M Trisodium Citrate Solution
 Approximately, 1.471 g of trisodium citrate was weighed and dissolved in 50 mL ultrapure water and stored at room temperature (22° C.±3° C.).
Preparation of Citrate Buffer Solution (pH-4.5)
 47 mL of 0.1 M citric acid monohydrate solution and 53 mL of trisodium citrate solution was mixed pH of the solution was found to be 4.50.
Preparation of Ultrapure Water (pH-4.5)
 Required volume of ultrapure water (~75 mL) was taken and pH was adjusted to 4.5 using citrate buffer (pH-4.5). This water was used as a test media for determining the solubility of test/reference items.
Preparation of Stock Solution
 Stock solutions of concentration 1 mg/mL for test items/reference items was prepared in methanol. The stock solution will be used for preparation of calibration curve standards.
Preparation of Calibration Curve
 Calibration curve of test/reference items was prepared by serially dilution consisting of 4-5-6 concentrations in 96 well format. Standard concentrations of 500 μg/mL, 200 μg/mL, 50 μg/mL, 12.5 μg/mL and 3.125 μg/mL were included.
 Methanol stock solution of 1 mg/mL concentration was prepared for test/reference items.
 The initial concentration of 500 μg/mL was prepared by adding 112.5 μL from a stock solution of 1 mg/mL to first well of a 96 well plate in duplicates and diluted with 112.5 μL of Ultrapure water (pH-4.5).

Similarly, a concentration of 200 µg/mL was prepared by adding 60 µL of 1 mg/mL methanol stock, 90 µL of methanol, 150 µL of Ultrapure water (pH-4.5) to the following wells in duplicates.

To the rest of the wells, 225 µL of vehicle (methanol: ultrapure water; 50:50) was added.

75 µL of 200 µg/mL solution was serially diluted.

The last two wells of each row was considered as blank.

The plate was incubated 22° C.±3° C. and 300 rpm for 30 minutes.

After incubation 100 µL of the incubated sample was transferred to an UV plate for UV analysis.

The plate was scanned from 200-400 nm to obtain Amax (absorbance maximum).

Solubility Testing by Shake Flask Method

The solubility of test items were determined at a highest test concentration of 1% w/v (10 mg/mL).

40 mg of test items were weighed into tubes.

4 mL of Ultrapure water was added to all tubes to get a concentration of 10 mg/mL (1% w/v).

The initial pH of the solubility samples were recorded. Then the pH of the solubility samples were adjusted to 4.5 using citrate buffer and vortexed. Then, the solution were observed visually for any precipitation.

After adjusting pH to 4.5, the test items which were found to be insoluble were diluted further with water and observed for solubility ensuring that the pH of the water is maintained at 4.5 until solubility (no visual precipitation) was observed.

The visually soluble samples were centrifuged at 10000 rpm for 10 minutes at room temperature (22° C.±3° C.).

An aliquot of the supernatant were diluted with equal volume of methanol. The samples were further diluted in methanol: water (50:50) to obtain dilution of 1:2, 1:4, 1:16, 1:32 etc.

The samples were then transferred to UV plate and scanned at Amax of that particular test/reference item.

Anti-Bacterial and Anti-Fungal Minimum Inhibitory Concentration (MIC) Method

Method: Microbroth Dilution Method (96-well format).

Solvent: Sterile MilliQ water and 0.1 M Citrate Buffer pH 4.5

Media used:

Bacterial: Cation-Adjusted Mueller-Hinton Broth (CAMHB)

Fungi: RPMI-1640

Bacteria

Incubation Temperature: 37° C.

Incubation Time: 24 hours

Inoculum Size: 5×10(5) cfu/mL

Strains:
  Staphylococcus aureus (ATCC 6538)
  Escherichia coli (ATCC 8739)
  Pseudomonas aeruginosa (ATCC 9027)
  Burkholderia cepacia (ATCC 25416)

Fungi:

Incubation Temperature:
  25° C. (*Candida albicans*)
  35° C. (*Aspergillus brasiliensis*)

Incubation Time: 48 hours

Inoculum Size: $5 \times 10^4$ cfu/mL

Strains:
  Candida albicans (ATCC 10231)
  Aspergillus brasiliensis (ATCC 16404)

End point: Inhibition of growth, Spectrophotometer Reading @ 600 nm

Reference standards: Benzoic acid, Ciprofloxacin (for bacteria) & Fluconazole (for fungi)

QC strains
  Escherichia coli (ATCC 25922) tested against Ciprofloxacin
  Candida parapsilosis (ATC 22019) tested against Fluconazole Test Compound Preparation:

Initially, a 10 mg/mL concentration of each test compound was prepared with MilliQ water and pH was checked. pH was adjusted for all compounds to 4.5 with citrate buffer (pH 4.5). For test compounds with solubility of less than 10 mg/mL, a saturated stock solution was used instead. All solubilized and pH 4.5-adjusted test compounds were filter-sterilized before subjecting to MIC study. Positive control was also dissolved in the similar way. For MIC an aliquot of 200 µL from the above stock was dispensed into 96-well plate and further 1:1 diluted.

Maintenance of strain:

Tester strains listed above were retrieved from −80° C. freezer and were thawed out. All the strains were inoculated on their respective agar medium and incubated under conditions/durations detailed above.

Preparation of inoculum:

The bacterial colony suspension in 0.85% saline was adjusted to 1 McFarland's standard using Densimat which was further diluted to 1:100 in CAMHB. The fungal suspension for inoculation was prepared in 0.85% saline from 6 days old culture (for mold, *A. brasiliensis*) and from 2 days old culture (for yeast, *C. albicans*) from Sabouraud Dextrose agar medium. Culture was scrapped/scooped from the plate, suspended in saline and the spores/cells counted using haemocytometer to provide a final inoculum of $5 \times 10^4$ cfu/mL.

96-well Plate Preparation:

Minimum inhibitory concentration (MIC) is performed to determine potency of test compounds along with standard antibiotics against bacterial strains. Micro titer plates were prepared as per the CLSI recommendations. One hundred and seventy five microliters of Cation-adjusted Muller Hinton Broth (CAMHB) was added to the first column of a 96 well flat bottom plate, which is the media control. Second column is for the stocks of the test compounds and reference standards from which dilutions are made. Then 175 µL of CAMHB was added to the 5th, 8th and 11th columns, 75 µL of CAMHB to the 4th, 7th and 10th columns and 50 µL of CAMHB to the 3rd, 6th and 9th columns and the last column was the organism control.

Antimicrobial Efficacy Testing

The Antimicrobial Efficacy Testing discussed herein was completed pursuant to the standard antimicrobial effectiveness test from Chapter 51 of the United States Pharmacopeia (USP 51), in which an antimicrobial composition can be tested against at least five microorganisms, including bacteria and fungi. In the Antimicrobial Efficacy Testing conducted herein, the following bacteria were utilized: *Staphylococcus aureus, Escherichia coli, Pseudomonas aeruginosa,* and *Burkholderia cepacia;* and the following fungi were utilized: *Candida albicans,* and *Aspergillus brasiliensis*. While one of ordinary skill in the art could replicate such Antimicrobial Efficacy Testing by completing USP 51 protocol, a brief summary was that each antimicrobial composition sample was tested against each microorganism being held at room temperature over the course of 28 days, with each sample being evaluated at specific intervals at the beginning of the Testing (initial), day 7, day 14, and day 28. The test sample colonies were counted at each interval to determine the number of surviving microorganisms. The log reduction of each microorganism at each interval was reported. The effectiveness of the antimicrobial agent sample was based on the USP 51 passing criteria.

Embodiments

Embodiment 1: A method for inhibiting microbial growth in a product, the method comprising: providing a composition including an antimicrobial agent, the antimicrobial agent comprising a dihydroxamic acid including a carbon chain length that is less than or equal to 7; applying the composition to the product to inhibit microbial growth.

Embodiment 2: The method of embodiment 1, wherein the antimicrobial agent comprises a MIC efficacy level of less than 1.0% according to the Minimum Inhibitory Concentration Test against at least one of *Staphylococcus aureus, Escherichia coli, Burkholderia cepacia, Pseudomonas aeruginosa, Candida albicans,* and *Aspergillus brasiliensis.*

Embodiment 3: The method of embodiment 1 or 2, wherein the dihydroxamic acid comprises:

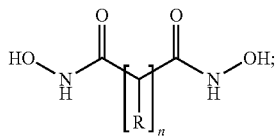

wherein n is a number between 0 and 5, inclusive, and R provides an R group, each R group being independently selected for each carbon and comprises any one of H, OH, $CH_3$, and any halogen.

Embodiment 4: The method of embodiment 3, wherein each R group provided in the dihydroxamic acid is either H or OH.

Embodiment 5: The method of embodiment 3 or 4, wherein n is less than or equal to 4 such that the carbon chain length is less than or equal to 6.

Embodiment 6: The method of embodiment 3 or 4, wherein n equals 2 such that the carbon chain length is 4.

Embodiment 7: The method of embodiment 1, wherein the antimicrobial agent comprises N, N', 2-trihydroxy butane diamide, N, N'-dihydroxysuccinamide, and combinations thereof.

Embodiment 8: The method of any one of the preceding embodiments, wherein the antimicrobial agent forms between about 0.001 to about 1.0% by weight of the composition.

Embodiment 9: The method of any one of the preceding embodiments, wherein the composition further comprises a carrier and a surfactant, and wherein the carrier comprises water, and wherein water comprises between about 50.0 to about 99.9% by weight of the composition.

Embodiment 10: The method of embodiment 9, wherein water comprises between about 90.0 to about 99.9% by weight of the composition.

Embodiment 11: The method of any one of the preceding embodiments, wherein the composition is substantially free of a traditional antimicrobial agent.

Embodiment 12: The method of any one of embodiments 1-10, wherein the composition further comprises a combinatorial antimicrobial agent.

Embodiment 13: The method of any one of the preceding embodiments, wherein the product is a wet wipe.

Embodiment 14: A wet wipe comprising: a substrate; and a wetting composition applied to the substrate, the wetting composition comprising: a carrier, the carrier comprising water, and water comprises between 85.0 to about 99.9% by weight of the wetting composition; a surfactant; and an antimicrobial agent, the antimicrobial agent comprising a dihydroxamic acid including a carbon chain length that is less than or equal to 7.

Embodiment 15: The wet wipe of embodiment 14, wherein the dihydroxamic acid comprises:

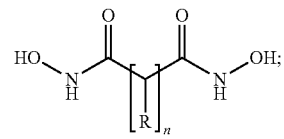

wherein n is a number between 0 and 5, inclusive, and R provides an R group, each R group being independently selected for each carbon and comprises any one of H, OH, $CH_3$, and any halogen.

Embodiment 16: The wet wipe of embodiment 15, wherein each R group provided in the dihydroxamic acid is either H or OH.

Embodiment 17: The wet wipe of embodiment 15 or 16, wherein n is less than or equal to 4 such that the carbon chain length is less than or equal to 6.

Embodiment 18: The wet wipe of embodiment 15 or 16, wherein n equals 2 such that the carbon chain length is 4.

Embodiment 19: The wet wipe of embodiment 14, wherein the antimicrobial agent comprises N, N', 2-trihydroxy butane diamide, N, N'-dihydroxysuccinamide, and combinations thereof.

Embodiment 20: The wet wipe of any one of embodiments 14-19, wherein the wetting composition is substantially free from a traditional antimicrobial agent, and wherein the wetting composition passes the Antimicrobial Efficacy Test as described herein.

Embodiment 21: The wet wipe of any one of embodiments 14-20, wherein the antimicrobial agent forms between about 0.001 to about 1.0% by weight of the wetting composition.

Embodiment 22: The wet wipe of any one of embodiments 14-21, wherein the water comprises between about 90.0 to about 99.9% by weight of the wetting composition.

Embodiment 23: The wet wipe of any one of embodiments 14-22, wherein the wetting composition is applied to the substrate at an add-on of between about 30% to about 400%.

Embodiment 24: The wet wipe of any one of embodiments 14-23, wherein the viscosity of the wetting composition is less than 500 cP.

Embodiment 25: An emulsion comprising a water phase and an oil phase, the emulsion comprising: water; an oil; and an antimicrobial agent, the antimicrobial agent comprising a dihydroxamic acid including a carbon chain length that is less than or equal to 7.

Embodiment 26: The emulsion of embodiment 25, wherein the dihydroxamic acid comprises:

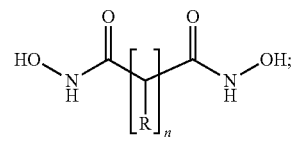

wherein n is a number between 0 and 5, inclusive, and R provides an R group, each R group being independently selected for each carbon and comprises any one of H, OH, CH$_3$, and any halogen.

Embodiment 27: The emulsion of embodiment 25 or 26, wherein water comprises between about 60% to about 95% by weight of the emulsion.

Embodiment 28: The emulsion of embodiment 25, wherein the antimicrobial agent comprises N, N', 2-trihydroxy butane diamide, N, N'-dihydroxysuccinamide, and combinations thereof.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A method for inhibiting microbial growth in a product, the method comprising:

providing a composition including an antimicrobial agent, the antimicrobial agent comprising N, N', 2-trihydroxy butane diamide and a cLogP value less than 0.50;

applying the composition to the product to inhibit microbial growth, wherein the antimicrobial agent comprises a MIC efficacy level of less than 1.0% according to the Minimum Inhibitory Concentration Test against at least one of *Staphylococcus aureus, Escherichia coli, Burkholderia cepacia, Pseudomonas aeruginosa, Candida albicans*, and *Aspergillus brasiliensis*.

2. The method of claim 1, wherein the antimicrobial agent forms between about 0.001 to about 1.0% by weight of the composition.

3. The method of claim 1, wherein the composition further comprises a carrier and a surfactant, and wherein the carrier comprises water, and wherein water comprises between about 50.0 to about 99.9% by weight of the composition.

4. The method of claim 3, wherein water comprises between about 90.0 to about 99.9% by weight of the composition.

5. The method of claim 1, wherein the composition further comprises an additional antimicrobial agent.

6. The method of claim 1, wherein the product is a wet wipe.

* * * * *